(12) United States Patent
Akula et al.

(10) Patent No.: US 8,513,016 B2
(45) Date of Patent: Aug. 20, 2013

(54) METHODS FOR PRODUCING TRANSGENIC PLANTS

(75) Inventors: Anisha Akula, Madison, WI (US); David R. Duncan, St. Charles, MO (US); Brenda A. Lowe, Mystic, CT (US); Michael T. Mann, Dardenne Prairie, MO (US); William L. Petersen, Roxbury, WI (US); Jyoti R. Rout, Niantic, CT (US); David D. Songstad, Ballwin, MO (US); Joel B. Wilks, East Hampton, CT (US); Wanggen Zhang, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/355,312

(22) Filed: Jan. 20, 2012

(65) Prior Publication Data

US 2012/0180166 A1 Jul. 12, 2012

Related U.S. Application Data

(62) Division of application No. 11/848,554, filed on Aug. 31, 2007, now Pat. No. 8,124,411.

(60) Provisional application No. 60/841,519, filed on Aug. 31, 2006.

(51) Int. Cl.
*C12N 5/00* (2006.01)

(52) U.S. Cl.
USPC ........... 435/420; 435/410; 435/412; 435/424; 435/430.1; 435/431; 800/295

(58) Field of Classification Search
USPC .............. 435/410, 412, 420, 424, 430.1, 431, 435/295; 800/295
See application file for complete search history.

(56) References Cited

U.S. PATENT DOCUMENTS

| | | | |
|---|---|---|---|
| 5,159,135 A | 10/1992 | Umbeck | 800/205 |
| 5,563,055 A | 10/1996 | Townsend et al. | 435/172.3 |
| 5,569,834 A | 10/1996 | Hinchee et al. | 800/205 |
| 5,591,616 A | 1/1997 | Hiei et al. | 435/172.3 |
| 5,767,368 A | 6/1998 | Zhong et al. | 435/172.3 |
| 5,886,244 A * | 3/1999 | Tomes et al. | 800/293 |
| 5,981,840 A | 11/1999 | Zhao et al. | 800/294 |
| 6,140,555 A | 10/2000 | Reichert et al. | 800/293 |
| 6,329,571 B1 | 12/2001 | Hiei | |
| 6,420,630 B1 | 7/2002 | Wilson et al. | 800/294 |
| 6,455,761 B1 | 9/2002 | Kuvshinov et al. | 800/294 |
| 7,429,691 B2 | 9/2008 | Zhang et al. | |
| 7,682,829 B2 | 3/2010 | Cai et al. | 435/469 |
| 7,939,325 B2 | 5/2011 | Adams, Jr. et al. | |
| 8,124,411 B2 | 2/2012 | Akula et al. | |
| 2003/0082580 A1 | 5/2003 | Engler et al. | 800/278 |
| 2004/0210959 A1 | 10/2004 | Armstrong et al. | 800/278 |
| 2004/0244075 A1 | 12/2004 | Cai et al. | 800/294 |
| 2006/0174367 A1 | 8/2006 | Zhang et al. | |
| 2008/0057512 A1 | 3/2008 | Rout et al. | 800/278 |
| 2008/0118981 A1 | 5/2008 | Akula et al. | |
| 2008/0124727 A1 | 5/2008 | Rout et al. | 800/278 |
| 2011/0162112 A1 | 6/2011 | Li et al. | |
| 2011/0212525 A1 | 9/2011 | Adams, Jr. et al. | |

FOREIGN PATENT DOCUMENTS

| | | |
|---|---|---|
| CN | 1206435 A | 1/1999 |
| EP | 0 672 752 | 9/1995 |
| EP | 0 897 013 | 2/1999 |
| EP | 0897013 A1 | 2/1999 |
| JP | 10-117776 | 5/1998 |
| JP | 2003-47463 | 2/2003 |
| JP | 2006-508681 | 3/2006 |
| WO | WO 95/06127 | 3/1995 |
| WO | WO 95/06128 | 3/1995 |
| WO | WO 97/41228 | 11/1997 |
| WO | WO 97/48814 | 12/1997 |
| WO | WO 98/51806 | 11/1998 |
| WO | WO 02/37951 | 5/2002 |
| WO | WO 02/102979 | 12/2002 |
| WO | WO 2004/052085 A1 | 6/2004 |
| WO | WO 2006/011959 | 2/2006 |
| WO | WO 2008/028119 | 3/2008 |
| WO | WO 2008/028121 | 3/2008 |

OTHER PUBLICATIONS

Wan et al. "Type I callus as a bombardment target for generating fertile transgenic maize (*Zea mays* L.)," Planta (1995) 196: 7-14.*
Kamo et al. "Embryogenic callus formation from maize protoplasts," Planta (1987) 172: 245-251.*
Akula et al., "High-yielding repetitive somatic embryogenesis and plant recovery in a selected tea clone, 'TRI-2025', by temporary immersion," *Plant Cell Reports*, 19:1140-1145, 2000.
Cheng et al., "Desiccation of plant tissues post-agrobacterium infection enhances T-DNA delivery and increases stable transformation efficiency in wheat," *In Vitro Cell Dev. Biol. Plant*, 39:595-604, 2003.
Dodds et al. "Experiments in Plant Tissue Culture," p. 240, 1999.
English translation of office action dated Sep. 16, 2010, in Chinese Patent Application No. 200780040000.2.
Espinoza et al., "Production of pineapple transgenic plants assisted by temporary immersion bioreactors," *Plant Cell Rep.*, 21:136-140, 2002.
Etienne et al., "Bioreactors in coffee micropropagation," *Brazilian Journal of Plant Psychology*, vol. 18(1), pp. 45-54, 2006.
Etienne et al., "Temporary immersion systems in plant micropropagation," *Plant Cell, Tissue and Organ Culture*, 69:215-231, 2002.
Frame et al., "*Agrobacterium tumefaciens*-mediated transformation of maize embryos using a standard binary vector system," *Plant Physiol.*, 129:13-22, 2002.
Fromm et al., "Inheritance and expression of chimeric genes in the progeny of transgenic maize plants," *Bio/Technology*, 8:833-839, 1990.

(Continued)

*Primary Examiner* — Susan McCormick Ewoldt

(74) *Attorney, Agent, or Firm* — Dentons US LLP; Thomas P. McBride Esq.

(57) ABSTRACT

A method of producing a stably transformed corn plant in a single container is demonstrated. This method allows for the automation of the transformation process and reduces labor, material, and ergonomic costs associated with traditional plant tissue culture systems.

2 Claims, 1 Drawing Sheet

(56) References Cited

OTHER PUBLICATIONS

Hanhineva et al., "Shoot regeneration from leaf explants of five strawberry (fragaria x ananassa) cultivars in temporary immersion bioreactor system," *In Vitro Cell, Dev. Biol.—Plant*, 41:826-831, 2005.

Ishida et al., "High efficiency transformation of maize (*Zea mays* L.) mediated by *Agrobacterium tumefaciens*," *Nature Biotech*, 14:745-750, 1996.

Kovacs et al., "Monitoring of haploid maize cell suspension culture conditions in bioreactors," *Plant Cell. Tissue and Organ Culture*, vol. 43, pp. 123-126, 1995.

Levy et al., "Transient agrobacterium-mediated gene expression in the arabidopsis hydroponics root system for subcellular localization studies," *Plant Mol. Biol. Reporter*, 23:179-184, 2005.

Mitshali et al., "In vitro culture of sugarcane in a liquid temporary immersion system and assessment of potential use in transgenesis," *South African J. of Botany*, 70(2):362-363, 2004.

Mtshali et al., "In vitro culture of sugarcane in a liquid temporary immersion system and assessment of potential use in transgenesis," *30th Annual Congress of the South African Association of Botanists*, Durban, Sout Africa, Jan. 19-22, 2004.

Murashige & Skoog, "A Revised Medium for Rapid Growth and Bio Assays with Tobacco Tissue Cultures," *Physiol. Plant.* 15:473-497, 1962.

Pental et al., "Somatic hybridisation using a double mutant of nicotiana tabacum," *Heredity*, vol. 53(1), pp. 79-83, 1984.

Sairam et al., "Shoot meristem: an ideal explant for *Zea mays* L. transformation," *Genome*, 46:323-329, 2003.

Skoog et al., "Chemical regulation of growth and organ formation in plant tissues cultured in vitro," *Symposia of the Society for Experimental Biology*, No. XI, Cambridge University Press, New York, 1957.

Snyman et al."Direct Somatic Embryogenesis for rapid, Cost Effective Production of Transgenic Sugarcane (*Saccharum* spp. Hybrids)," *Proc S Afr Sug Technol Assoc*, 47:186-187, 2000.

Sticklen et al."Invited Review: Shoot Apical Meristem: A sustainable explant for genetic transformation of cereal crops," *In Vitro Cell. Dev. Biol. Plant*, 41:1870200, May-Jun. 2005.

Toki et al."Early infection of scutellum tissue with agrobacterium allows hig-speed transformation of rice," *Plant J.*, 47(6):969-976, 2006.

Zhao et al., "High throughput genetic trasformation mediated by *Agrobacterium tumefaciens* in maize," *Molecular Breeding*, 8:323-333, 2001.

Gordon-Kamm et al., "Transformation of Maize Cells and Regeneration of Fertile Transgenic Plants," *The Plant Cell*, ; vol. 2; pp. 603-618; Jul. 1990.

Zhong et al., In-vitro morphogenesis of corn (*Zea mays* L.—I. Differentiation of multiple , shoot clumps and somatic embryos from shoot tips, *Planta*, 187:483-489, 1992.

English translation of office action issued in Japanese Application No. 2009-526926 on Dec. 11, 2012.

Radojevic, "Tissue culture of Maize *Zea mays* <<Cudu>> I. Somatic Embryogenesis in the Callus Tissue," *Plant Physiol.* 119:435-441, 1985.

* cited by examiner

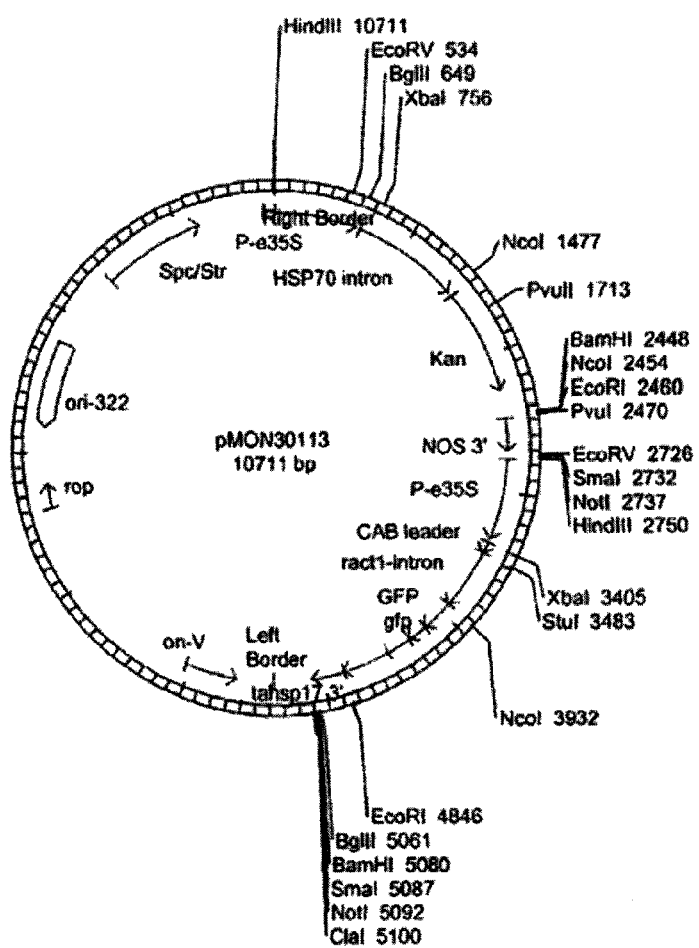

ously automated. In micropropagation, an explant

METHODS FOR PRODUCING TRANSGENIC PLANTS

This application is a divisional of U.S. application Ser. No. 11/848,554, filed Aug. 31, 2007 now U.S. Pat. No. 8,124,411, which application claims benefit of the priority of U.S. provisional application Ser. No. 60/841,519, filed Aug. 31, 2006, each of the entire disclosures of which are incorporated herein by reference.

BACKGROUND OF THE INVENTION

Field of the Invention

Micropropagation of plants has been done routinely in large batches and automated. In micropropagation, an explant is usually taken up and placed in one regeneration media that must be kept fresh for the duration of the regeneration process to produce a series of plants. This is in contrast to transformation processes, which are designed to produce new transgenic events, and requires integration of foreign DNA into a plant cell. Automating the plant tissue culture process, particularly the transformation process, has been difficult. The plant tissues go through different stages that require different kinds of growth media and conditions. Transformation processes require multiple steps and multiple media. For example, in *Agrobacterium*-mediated transformation, the process starts with the isolation of an explant that is regenerable and transformable. Then the explant is inoculated with *Agrobacterium* in an inoculation media. After inoculation, excess *Agrobacterium* is typically removed and the explant and the *Agrobacterium* are co-cultured together to allow the transfer of DNA. After co-culture, the presence of the *Agrobacterium* is deleterious to plant tissue culture (for example, causes unwanted contamination during subsequent handling and tissue culture steps), so typically the explants are moved to fresh medium containing antibiotics to inhibit the growth of the *Agrobacterium*. This medium may or may not contain selection agents. If it does not, then it is called delay or resting medium. Explants may be placed on delay medium to allow for some time to grow before optionally being placed on selection medium. Other protocols place the explants directly into selection media for selection of transgenic events. Selection regimes vary widely depending upon the selection agent and the explant system. Often multiple steps of selection are used and varying amounts of selection agent can be necessary in the different steps. After selection of the transgenic events, the living transgenic events are then moved to regeneration media for regeneration to plantlets that can then be moved to soil. Up to the present time, transformation processes have been time-consuming and laborious and not able to be done on a large scale. Automating transformation process would allow for large numbers of transgenic plants to be produced with reduced labor, material, and ergonomic burden.

The present invention has overcome the previous limitations in transformation by providing methods and apparatus that perform some or all of the transformation steps, and optionally some of the regeneration steps, in a single container. Thus, the present methods overcome the deficiencies of current transformation protocols by eliminating time-consuming steps required for sub-culturing plant tissue and changing media. The methods and apparatus are particularly suitable for transformation automation, regeneration automation, and/or large-scale production of transformed cells, tissues, and plants.

The invention of genomics has enabled identification and isolation of a large number of genes and has necessitated the need for reliable and efficient high throughput transformation production systems for testing the utility of these genes by transforming them into economically important crops such as corn. Current corn transformation methods requires, at least, four transfer steps from the step of selecting a transformed cell to the step of transferring transgenic plants to soil thereby requiring higher material costs, for example, culture plates and media, and labor costs. Several manual transfers of tissues also elevate the risk of ergonomic injury due to repeated motions.

Thus, there is a need in the art of corn transformation for a high throughput automated system for plant transformation, selection, and regeneration which can produce a large number of transgenic plants for testing genes and creating useful plants while lowering material and labor costs. There is also a need in the art for methods that can lower risk of ergonomic injuries making the work place safer.

Herein, the inventors provide a corn transformation method for selecting and regenerating transformed corn plants suitable for high throughput automation system. The method employs a suitable support matrix in combination with liquid selection and regeneration medium. Use of this liquid culture method eliminates the need for multiple transfers that are normally required when using solid medium for selection and regeneration steps. Further, this method enables advance regeneration which has been a problem in liquid culture medium so far. Still further, the step of selecting a transformed cell and regeneration can be achieved in a single container such as a sundae cups until plants are transferred to soil.

SUMMARY OF THE INVENTION

The present invention provides novel methods for automating plant transformation processes by providing a method of stably transforming, and optionally selecting and partially regenerating a plant in a container. In some embodiments, a single container may be used to perform the methods of the present invention. In other embodiments, multiple containers (for example, a system of interconnected vessels) may be provided for ease of use and optimization of the present invention.

In one aspect of the invention, method for producing a transgenic corn plant is provided. The method comprises obtaining a transformable corn explant; transforming the transformable corn explant; selecting a transformed corn cell from the transformable corn explant on a selection medium; and regenerating the transformed cell into a plant on a regeneration medium, wherein transforming, selecting, and regenerating are done in the same container. Optionally, the selection in the container may be omitted, and the transgenic plantlet or transgenic plant may be subject to selection after being placed into soil (for example, sprayed with a selective agent).

The container may be a bioreactor, Petri plate, multi-well plate, flask, jar, bottle, jug, PlantCon™, temporary emersion system, and a combination thereof and is provided with a means for providing and removing the medium. In some embodiments, the container is a Petri plate, multi-well plate, PlantCon, or temporary emersion system.

The explant may be selected from the group consisting of a callus, embryo, and a cell suspension.

The medium may be a liquid medium, solid medium, or a combination thereof. In an embodiment, the selection medium is a solid medium and regeneration medium is a liquid medium overlaid over the solid selection medium.

The explant may be contacted with the medium temporarily. In an embodiment, the explant is contacted with the selection medium and the regeneration medium for about 1 to about 5 minutes about every 12 to 24 hours.

In yet another aspect of the present invention, a method for obtaining explant for producing a transgenic corn plant is provided. The method comprises dividing a callus into smaller callus pieces. In an embodiment, the callus is a type I callus.

In yet another aspect of the present invention, a method for preparing *Agrobacterium* cell suspension for inoculating an explant is provided. The method comprises culturing a frozen glycerol stock of *Agrobacterium* directly into an induction medium.

In yet another aspect of the present invention, a corn cell culture comprising transformable and embryogenic cells is provided.

In yet another aspect of the present invention, a method for producing a corn transformable and embryogenic cell culture is provided. The method comprises obtaining a callus from corn embryos and culturing the callus for about 5 days to 30 days in a liquid medium to produce the cell culture. In an embodiment, the callus is a type II callus.

BRIEF DESCRIPTION OF DRAWINGS

FIG. 1 Exemplary plasmid map of pMON30113.

DETAILED DESCRIPTION

The following definitions will aid in the understanding of the description of the invention.

"Callus" refers to a dedifferentiated proliferating mass of cells or tissue.

"Explant" refers to a plant part that is capable of being transformed and subsequently regenerated into a transgenic plant. Typical explants include immature embryos, callus, cotyledons, meristems, leaves, or stems.

"Tissue culture media" refers to liquid, semi-solid, or solid media used to support plant growth and development in a non-soil environment. Suitable plant tissue culture media is known to one of skill in the art, as discussed in detail subsequently. The media components can be obtained from suppliers other than those identified herein and can be optimized for use by those of skill in the art according to their requirements.

"Coding sequence", "coding region" or "open reading frame" refers to a region of continuous sequential nucleic acid triplets encoding a protein, polypeptide, or peptide sequence.

"Endogenous" refers to materials originating from within the organism or cell.

"Exogenous" refers to materials originating from outside of the organism or cell. It refers to nucleic acid molecules used in producing transformed or transgenic host cells and plants. As used herein, exogenous is intended to refer to any nucleic acid that is introduced into a recipient cell, regardless of whether a similar nucleic acid may already be present in such cell.

"Genome" refers to the chromosomal DNA of an organism. The genome is defined as a haploid set of chromosomes of a diploid species. For the purposes of this application, genome also includes the organellar genome.

"Monocot" or "monocotyledonous" refers to plants having a single cotyledon. Examples include cereals such as maize, rice, wheat, oat, and barley.

"Nucleic acid" refers to deoxyribonucleic acid (DNA) or ribonucleic acid (RNA).

"Phenotype" refers to a trait exhibited by an organism resulting from the interaction of genotype and environment.

"Polyadenylation signal" or "polyA signal" refers to a nucleic acid sequence located 3' to a coding region that promotes the addition of adenylate nucleotides to the 3' end of the mRNA transcribed from the coding region.

"Promoter" or "promoter region" refers to a nucleic acid sequence, usually found 5' to a coding sequence, that controls expression of the coding sequence by controlling production of messenger RNA (mRNA) by providing the recognition site for RNA polymerase or other factors necessary for the start of transcription at the correct site.

"Recombinant nucleic acid vector" or "vector" refers to any agent such as a plasmid, cosmid, virus, autonomously replicating sequence, phage, or linear or circular single- or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid vectors or constructs are capable of introducing a 5' regulatory sequence or promoter region and a DNA sequence for a selected gene product into a cell in such a manner that the DNA sequence is transcribed into a functional mRNA, which is subsequently translated into a polypeptide or protein.

"Regeneration" refers to the process of growing a plant from a plant cell.

"Regeneration medium" refers to a plant tissue culture medium required for containing a selection agent.

"Regenerable callus" refers to callus from which whole plants can be produced but where the mode of regeneration (embryogenesis or organogenesis) has not been determined or is not pertinent to the discussion.

"Selectable marker" or "screenable marker" refers to a nucleic acid sequence whose expression confers a phenotype facilitating identification of cells containing the nucleic acid sequence.

"Selection" refers to contacting an inoculated explant with a selection medium for obtaining a transformed cell, tissue, or plant.

"Selection medium" refers to a plant tissue culture medium containing a selection agent.

"Transcription" refers to the process of producing an RNA copy from a DNA template.

"Transformation" refers to a process of introducing an exogenous nucleic acid sequence (vector or construct) into a cell or protoplast, in which that exogenous nucleic acid is incorporated into the nuclear DNA, plastid DNA, or is capable of autonomous replication.

"Transgenic" refers to organisms into which an exogenous nucleic acid sequence has been integrated.

"Transformable explant" refers to any part of a plant that is receptive to transformation.

The present invention provides a system in which stable transformation can be carried out in a single container. The transformation process begins with inoculation of the transformable explant with *Agrobacterium* and results in a stably transformed plantlet with roots suitable for transfer to soil.

There are many containers that can be used for this purpose. Bioreactors, including the temporary immersion system, can be used. Many different containers have been used for plant liquid tissue culture, including, but not limited to, Petri plates of various sizes, multi-well plates, flasks, jars, bottles, jugs, and PlantCons. These containers are usually provided with means such as an inlet and outlet for providing the fresh medium and removing the expensed medium. A plurality of containers may be connected to obtain a high-throughput system.

These containers may include some support for the explant. That support can be, but is not limited to, filter paper, felt, rafts, glass beads, zirconia/silica beads, foam, or solid media. Liquid media is usually placed in the container and then exchanged as needed. This exchange can be done manually or mechanically.

The containers may contain many explants at a time or may be small enough to contain a single explant. In the case of multi-well plates, an array of small wells each containing an explant is used to culture large numbers of explants. Advantages of the multi-well plates include the isolation of any contaminated explants. The explants may be prepared manually or mechanically.

The purpose of the invention is to have a system that is easily automatable from start to finish; however, any of these liquid culture systems and containers can be used in combination with other transformation, selection, and regeneration steps known to one of skill in the art.

A high throughput transformation system can be developed in which containers may be manipulated by robotic arms on a freely configurable work table that may include incubators and shakers in addition to standard lab ware. Various liquid handling tools equipped with one or more pipetting tips can be used to provide the fresh medium and remove the expensed medium. Work table, robotic arms, and the liquid handling tools can be controlled by software via a computer. Alternatively, liquid medium for selecting and regenerating the transformed cell can be provided to the container via one or more tube(s) connected to a medium storage vessel and removed via one or more tubes connected to a waste vessel. The provision and removal of the medium can be controlled manually or mechanically.

To initiate a transformation process in accordance with the present invention, it is first necessary to select genetic components to be inserted into the plant cells or tissues. Genetic components can include any nucleic acid that is introduced into a plant cell or tissue using the method according to the invention. Genetic components can include non-plant DNA, plant DNA or synthetic DNA.

In a preferred embodiment, the genetic components are incorporated into a DNA composition such as a recombinant, double-stranded plasmid or vector molecule comprising at least one or more of following types of genetic components: (a) a promoter that functions in plant cells to cause the production of an RNA sequence, (b) a structural DNA sequence that causes the production of an RNA sequence that encodes a product of agronomic utility, and (c) a 3' non-translated DNA sequence that functions in plant cells to cause the addition of polyadenylated nucleotides to the 3' end of the RNA sequence.

The vector may contain a number of genetic components to facilitate transformation of the plant cell or tissue and regulate expression of the desired gene(s). In one preferred embodiment, the genetic components are oriented so as to express an mRNA, which in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA.

Means for preparing plasmids or vectors containing the desired genetic components are well known in the art. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter". The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters would include but are not limited to the nopaline synthase (NOS) and octopine synthase (OCS) promoters that are carried on tumor-inducing plasmids of *Agrobacterium tumefaciens*, the caulimovirus promoters such as the cauliflower mosaic virus (CaMV) 19S and 35S promoters and the figwort mosaic virus (FMV) 35S promoter, the enhanced CaMV35S promoter (e35S), the light-inducible promoter from the small subunit of ribulose bisphosphate carboxylase (ssRUBISCO, a very abundant plant polypeptide). All of these promoters have been used to create various types of DNA constructs that have been expressed in plants.

Promoter hybrids can also be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive as described, and temporally regulated, spatially regulated, and spatio-temporally regulated. Other promoters that are tissue-enhanced, tissue-specific, or developmentally regulated are also known in the art and envisioned to have utility in the practice of this invention.

Promoters may be obtained from a variety of sources such as plants and plant DNA viruses and include, but are not limited to, the CaMV35S and FMV35S promoters and promoters isolated from plant genes such as ssRUBISCO genes. As described below, it is preferred that the particular promoter selected should be capable of causing sufficient expression to result in the production of an effective amount of the gene product of interest.

The promoters used in the DNA constructs (for example, chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes (see, for example U.S. Pat.

No. 5,362,865). Other genetic components that serve to enhance expression or affect transcription or translation of a gene are also envisioned as genetic components.

The 3' non-translated region of the chimeric constructs should contain a transcriptional terminator, or an element having equivalent function, and a polyadenylation signal that functions in plants to cause the addition of polyadenylated nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 0385 962).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In one preferred embodiment, the vector contains a selectable, screenable, or scoreable marker gene. These genetic components are also referred to herein as functional genetic components, as they produce a product that serves a function in the identification of a transformed plant, or a product of agronomic utility. The DNA that serves as a selection device functions in a regenerable plant tissue to produce a compound that would confer upon the plant tissue resistance to an otherwise toxic compound. Genes of interest for use as a selectable, screenable, or scorable marker would include but are not limited to GUS, green fluorescent protein (GFP), anthocyanin biosynthesis related genes (C1, Bperu), luciferase (LUX), antibiotics like kanamycin (Dekeyser et al., 1989), and herbicides like glyphosate (Della-Cioppa et al., 1987). Other selection devices can also be implemented including but not limited to tolerance to phosphinothricin, bialaphos, dicamba, and positive selection mechanisms and would still fall within the scope of the present invention.

The present invention can be used with any suitable plant transformation plasmid or vector containing a selectable or screenable marker and associated regulatory elements as described, along with one or more nucleic acids expressed in a manner sufficient to confer a particular trait. Examples of suitable structural genes of agronomic interest envisioned by the present invention would include but are not limited to genes for insect or pest tolerance, herbicide tolerance, genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms (see for example, Bird et al., 1991). The RNA could also be a catalytic RNA molecule (for example, a ribozyme) engineered to cleave a desired endogenous mRNA product (see for example, Gibson and Shillitoe, 1997). More particularly, for a description of anti-sense regulation of gene expression in plant cells see U.S. Pat. No. 5,107,065 and for a description of gene suppression in plants by transcription of a dsRNA see U.S. Pat. No. 6,506,559, U.S. Patent Application Publication No. 2002/0168707 A1, and U.S. patent application Ser. Nos. 09/423,143 (see WO 98/53083), 09/127,735 (see WO 99/53050) and 09/084,942 (see WO 99/61631), all of which are incorporated herein by reference. Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet that one desires, for example, to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

The technologies for the introduction of DNA into cells are well known to those of skill in the art and can be divided into categories including but not limited to: (1) chemical methods; (2) physical methods such as microinjection, electroporation, and micro-projectile bombardment; (3) viral vectors; (4) receptor-mediated mechanisms; and 5) *Agrobacterium*-mediated plant transformation methods.

For *Agrobacterium*-mediated transformation, after the construction of the plant transformation vector or construct, said nucleic acid molecule, prepared as a DNA composition in vitro, is introduced into a suitable host such as *E. coli* and mated into another suitable host such as *Agrobacterium*, or directly transformed into competent *Agrobacterium*. These techniques are well-known to those of skill in the art and have been described for a number of plant systems including soybean, cotton, and wheat (see, for example U.S. Pat. Nos. 5,569,834 and 5,159,135, and WO 97/48814, herein incorporated by reference in their entirety).

The present invention encompasses the use of bacterial strains to introduce one or more genetic components into plants. Those of skill in the art would recognize the utility of *Agrobacterium*-mediated transformation methods. A number of wild-type and disarmed strains of *Agrobacterium tumefaciens* and *Agrobacterium rhizogenes* harboring Ti or Ri plasmids can be used for gene transfer into plants. Preferably, the *Agrobacterium* hosts contain disarmed Ti and Ri plasmids that do not contain the oncogenes that cause tumorigenesis or rhizogenesis, respectively, which are used as the vectors and contain the genes of interest that are subsequently introduced into plants. Preferred strains would include but are not limited to disarmed *Agrobacterium tumefaciens* strain C58, a nopaline-type strain that is used to mediate the transfer of DNA into a plant cell, octopine-type strains such as LBA4404 or succinamopine-type strains, for example, EHA101 or EHA105. Other bacteria such as *Sinorhizobium, Rhizobium,* and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector (Broothaerts et al, 2005).

The use of these strains for plant transformation has been reported and the methods are familiar to those of skill in the art.

The explants can be from a single genotype or from a combination of genotypes. Any corn seed that can germinate is a viable starting material. In a preferred embodiment, superior explants from plant hybrids can be used as explants. For example, a fast-growing cell line with a high culture response (higher frequency of embryogenic callus formation, growth rate, plant regeneration frequency, etc.) can be generated using hybrid embryos containing several genotypes. In a preferred embodiment, an F1 hybrid or first generation offspring of cross-breeding can be used as a donor plant and crossed with another genotype. Those of skill in the art are aware that heterosis, also referred to herein as "hybrid vigor", occurs when two inbreds are crossed. The present invention thus encompasses the use of an explant resulting from a three-way cross, wherein at least one or more of the inbreds is highly regenerable and transformable, and the transformation and regeneration frequency of the three-way cross explant exceeds the frequencies of the inbreds individually. Other tissues are also envisioned to have utility in the practice of the present invention. Explants can include mature embryos, immature embryos, meristems, callus tissue, or any other tissue that is transformable and regenerable.

Any suitable plant culture medium can be used during the transformation process. Examples of suitable media would include but are not limited to MS-based media (Murashige and Skoog, 1962) or N6-based media (Chu et al., 1975) supplemented with additional plant growth regulators including but not limited to auxins such as picloram (4-amino-3,5, 6-trichloropicolinic acid), 2,4-D (2,4-dichlorophenoxyacetic acid) and dicamba (3,6-dichloroanisic acid); cytokinins such as BAP (6-benzylaminopurine) and kinetin; ABA; and gibberellins. Other media additives can include but are not limited to amino acids, macroelements, iron, microelements, inositol, vitamins and organics, carbohydrates, undefined media components such as casein hydrolysates, ethylene antagonists including silver nitrate with or without an appropriate gelling agent such as a form of agar, such as a low melting point agarose or Gelrite® if desired. Those of skill in the art are familiar with the variety of tissue culture media, which when supplemented appropriately, support plant tissue growth and development and are suitable for plant transformation and regeneration. These tissue culture media can either be purchased as a commercial preparation or custom prepared and modified. Examples of such media would include but are not limited to Murashige and Skoog (1962), N6 (Chu et al., 1975), Linsmaier and Skoog (1965), Uchimiya and Murashige (1962), Gamborg's media (Gamborg et al., 1968), D medium (Duncan et al., 1985), McCown's Woody plant media (McCown and Lloyd, 1981), Nitsch and Nitsch (1969), and Schenk and Hildebrandt (1972) or derivations of these media supplemented accordingly. Those of skill in the art are aware that media and media supplements such as nutrients and growth regulators for use in transformation and regeneration and other culture conditions such as light intensity during incubation, pH, and incubation temperatures can be optimized for the particular variety of interest.

Once the transformable plant tissue is isolated, the next step of the method is introducing the genetic components into the plant tissue. This process is also referred to herein as "transformation." The plant cells are transformed and each independently transformed plant cell is selected. The independent transformants are referred to as transgenic events. A number of methods have been reported and can be used to insert genetic components into transformable plant tissue. Micro-projectile bombardment and *Agrobacterium*-mediated gene delivery are the two most commonly used plant transformation methods, but other methods are known.

Those of skill in the art are aware of the typical steps in the plant transformation process. Those of skill in the art are familiar with procedures for growth and suitable culture conditions for *Agrobacterium* as well as subsequent inoculation procedures. The density of the *Agrobacterium* culture used for inoculation and the ratio of *Agrobacterium* cells to explant can vary from one system to the next, and therefore optimization of these parameters for any transformation method is expected. *Agrobacterium* can also be induced directly from frozen stocks or can be cultured in multiple ways known to one of skill in the art.

The next stage of the transformation process is the inoculation. In this stage the explants and *Agrobacterium* cell suspensions are mixed together. This can be achieved by incubating explants in *Agrobacterium* cell suspension. In other embodiments described herein, the explants were inoculated while they were still attached to the donor tissue, while removing the explants from the donor tissue, after plating the explants onto the selection medium, or by a combination. The duration and condition of the inoculation and *Agrobacterium* cell density will vary depending on the plant transformation system.

After inoculation, any excess *Agrobacterium* suspension can be removed and the *Agrobacterium* and target plant material are co-cultured. The co-culture refers to the time post-inoculation and prior to transfer to a delay or selection medium. Any number of plant tissue culture media can be used for the co-culture step. Plant tissues after inoculation with *Agrobacterium* can be cultured in a liquid or a semi-solid media. The co-culture is typically performed for about one to three days at a temperature of about 18° C.-30° C. The co-culture can be performed in the light or in light-limiting conditions. Lighting conditions can be optimized for each plant system as is known to those of skill in the art.

After co-culture with *Agrobacterium*, the explants typically can be placed directly onto selective media. Alternatively, after co-culture with *Agrobacterium*, the explants could be placed on media without the selective agent and subsequently placed onto selective media. Those of skill in the art are aware of the numerous modifications in selective regimes, media, and growth conditions that can be varied depending on the plant system and the selective agent. Typical selective agents include but are not limited to antibiotics such as geneticin (G418), kanamycin, paromomycin or other chemicals such as glyphosate, phosphinothricin, bialaphos, and dicamba. Additional appropriate media components can be added to the selection or delay medium to inhibit *Agrobacterium* growth. Such media components can include, but are not limited to, antibiotics such as carbenicillin or cefotaxime.

In one embodiment, inoculation, co-culture and selection steps were combined into a single step by plating the inoculated explants directly onto a medium that contained selective agents for suppressing growth of *Agrobacterium* and killing non-transformed explant cells for improving transformation production system efficiency.

The cultures are subsequently transferred to a media suitable for the recovery of transformed plantlets. Those of skill in the art are aware of the number of methods to recover transformed plants. A variety of media and transfer requirements can be implemented and optimized for each plant system for plant transformation and recovery of transgenic plants. Consequently, such media and culture conditions disclosed in the present invention can be modified or substituted with nutritionally equivalent components, or similar processes for selection and recovery of transgenic events, and still fall within the scope of the present invention.

The present invention includes all of the previously described steps; however, modifications are made as appropriate to facilitate the process in a single container. Liquid culture on various types of support is used to facilitate changing the media from step to step. A temporary immersion system bioreactor or other device giving similar results can be used for media replacement.

In the case of callus as the explant, the callus can be minced using various devices including but not limited to a garlic press, scissors, scalpels, or other cutting devices. The callus can be minced very fine to fit into a small multi-well plate system, where the expectation is to obtain a single event in each well. These modifications provide ergonomic relief and can be used to recover many transgenic events from a single piece of callus.

The transformants produced are subsequently analyzed to determine the presence or absence of a particular nucleic acid of interest contained on the transformation vector. Molecular analyses can include but are not limited to Southern blots (Southern, 1975), or PCR (polymerase chain reaction) analyses, immunodiagnostic approaches, and field evaluations. These and other well known methods can be performed to confirm the stability of the transformed plants produced by the methods disclosed. These methods are well known to those of skill in the art and have been reported (see for example, Sambrook et al., 1989).

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Explant Source and Culture Conditions

Eight-day-old callus (eight days post sub-culture) obtained from immature embryos of corn was cultured on gelled 211V medium (N6 basal salt mixture, 1 mg/L 2-4-D, 1 mg/L Thiamine HCL, 1 mg/L Nicotinic Acid, 0.91 g/L L-Asparagine Monohydrate, 0.1 g/L myo-inositol, 0.5 g/L MES, 1.6 g/L $MgCl_2.6H_2O$, 0.1 g/L casein hydrolysate, 0.69 g/L Proline, 20 g/L sucrose, 0.1 mM silver nitrate, 6 g/L Phyta agar).

Wherever gelled medium use is mentioned, 25×100 mm Petri plates containing 50 mL of medium with 12 explants per plate were used and all transfers were done manually.

Liquid medium consisted of 212V (N6 basal salts with 2 mg/L 2-4-D, 1 mg/L Thiamine HCL, 1 mg/L Nicotinic Acid, 0.91 g/L L-Asparagine Monohydrate, 0.1 g/L myo-inositol, 0.5 g/L MES, 1.6 g/L $MgCl_2.6H_2O$, 0.1 g/L casein hydrolysate, 0.69 g/L Proline, 20 g/L sucrose, 0.01 mM silver nitrate, pH adjusted to 5.8 and autoclaved at 121° C. and 105 kPa for 20 min. Post autoclave, filter sterilized Carbenicillin and Paromomycin at 250 mg/L or 500 mg/L and 100 mg/L or 200 mg/L of concentration was added to the medium as a selective agent.

For liquid culture, either a Temporary Immersion System (TIS) vessel, 240×240 mm large Petri-plates, or 25×100 mm Petri-plates, or multi-well plates were used.

All cultures were incubated at 27-28° C. in the dark in a growth cabinet (Percival scientific Series 101 US).

*Agrobacterium Tumefaciens* Infection and Co-Cultivation.

Actively growing, uniform sized, eight-day-old callus was selected and inoculated with *Agrobacterium* suspension ($0.25×10^9$ cfu/mL) for 30 minutes. The calli were washed with 212V liquid medium containing 0.1 mM $AgNO_3$ and transferred to TIS container or 25×100 mm Petri plate containing filter paper or large shallow Petri-plate (240×240 mm) containing two layers of (220×220 mm) polyester felt. Co-cultivation treatments were carried out in the dark at 23° C.

*A. Tumefaciens* Strains and Plasmids.

ABI *Agrobacterium* strain C58 was used to mediate the transfer of DNA into the plant cells. The plasmid pMON30113 (FIG. 1) contained neomycin phosphotransferase II gene (NPTII) as the selectable marker and a green fluorescence protein gene (GFP) as the screenable marker driven by the 35S promoter.

Example 2

Temporary Immersion System (TIS)

A modified TIS was constructed as follows. Two chambers of an autoclavable 250 mL filter unit (Nalge Nunc Intl., Rochester, N.Y.) were connected by insertion of a glass tube into the base of the support plate normally used to hold the membrane filter. Air hoses were connected to the two chambers. The airflow was sterilized by passage through 0.2 μm pore size, 50 mm diameter hydrophobic PTFE membrane filters (Millipore, Billerica, Mass.). Liquid medium was placed in the lower chamber and explant materials were placed on a supporting disc in the upper chamber. Air was pumped into the lower chamber to displace the liquid medium through the glass tube to the upper chamber, immersing the callus. Air pumped to the upper chamber forced the medium to return to the lower chamber (only a thin film of liquid medium remains on the tissues). An electronic timer was used to operate solenoids that control airflow to either the upper or lower chamber. The timer was programmed for either airflow into the lower chamber, airflow to the upper chamber or "idle time" (no airflow). Airflow times were set at 1 to 5 min each while the idle time could vary. The program was then set to run in a continuous cycle through the different stages of the transformation process. In this way, tissues were completely immersed for approximately 1-5 min at set time intervals. This is called immersion cycle frequency.

Optimization of Immersion Cycle Frequencies.

Tissue was cultured at 1 min duration submersion and four different immersion cycle frequencies (once every 6 h, 8 h, 12 h and 24 h) each, for a period of 8 weeks were tested. As a control, half of the calli derived from the same ear were cultured on 211V gelled medium with selection.

The immersion time interval was found to significantly impact the proliferation rate of callus in the TIS. The maximum rate of calli proliferation and biomass increase occurred using an immersion frequency of either 12 h or 24 h. With these two immersion cycle frequencies, 70-80% of calli produced GFP positive sectors. By increasing the immersion frequency to one cycle every 6 or 8 hours, no sign of callus proliferation was observed and within 10 to 14 days, callus turned brown and eventually died.

Effect of Carbenicillin on *A. Tumefaciens* Growth.

Calli were inoculated with pMON30113 as described above. Following inoculation, the infected calli were transferred to callus proliferation medium (212V) supplemented with either 0, 100, 250, 500 or 1000 mg/L carbenicillin. Growth of *Agrobacterium* was visually evaluated by observing turbidity of the liquid medium in the lower chamber of the TIS apparatus. A separate TIS unit with non-inoculated control treatment was included. An additional control of non-inoculated callus was also cultured on gelled medium supplemented with carbenicillin (211V) to study the effect of carbenicillin on callus culture.

No significant difference in callus quality was noticed when non-inoculated callus cultured on 211V (gelled) and 212V (liquid) medium supplemented with or without carbenicillin, indicating that there is no negative effect of carbenicillin on growth and development of non-inoculated callus. However, differences in growth of *A. tumefaciens* and GFP-positive sectors were observed as the concentration of carbenicillin increased from 0.0 to 1000 mg/L. Carbenicillin at a concentration of 100 mg/L could not suppress the growth of *Agrobacterium* either in liquid or gelled medium. The optimum concentration of carbenicillin was found to be 500 mg/L for gelled and liquid medium Effect of Paromomycin on Calli and Shoot Proliferation.

To inhibit non-transgenic callus proliferation, both gelled (control) and liquid culture medium were supplemented with the selective agent paromomycin (25, 50, 75, 100, or 200 mg/L). Control treatments were (1) non-inoculated callus on selective medium, (2) non-inoculated callus on selection-free medium, and (3) inoculated callus on selection-free medium. The basic culture medium consisted of either 211V or 212V. For this experiment 25×100 mm deep Petri-plates were used. With liquid culture, two layers of 60×60 mm felt were used to hold the explants. The selective agent for *Agrobacterium*-inoculated culture contained carbenicillin and paromomycin.

Paromomycin at low concentrations more effectively inhibited embryogenic callus growth and plant regeneration in liquid medium than the gelled medium. No plants were obtained from non-inoculated callus from liquid medium containing as low as 50 mg/L of paromomycin whereas 50% of the callus produced plantlets on gelled medium at the same concentration of paromomycin. Paromomycin at a concentration of 100 mg/L inhibited callus growth with both liquid and gelled medium.

Optimization of Amount of Liquid Medium Used in TIS.

Developing callus was cultured in one of four different amounts of liquid medium (20 mL, 30 mL, 50 mL and 100 mL/container).

Selection and Regeneration in TIS.

After 3 days of co-culture in TIS, 20 mL of selection medium 212VRT (N6 basal salts with 2 mg/L 2,4-D, 1 mg/L Thiamine HCL, 1 mg/L Nicotinic Acid, 0.91 g/L L-Asparagine Monohydrate, 0.1 g/L myo-inositol, 0.5 g/L MES, 1.6 g/L $MgCl_2.6H_2O$, 0.1 g/L casein hydrolysate, 0.69 g/L Proline, 20 g/L sucrose, 0.01 mM silver nitrate, 500 mg/L Carbenicillin and 100 mg/L Paromomycin) was injected in lower chamber of TIS. Calli were immersed for one minute once every 12 hours. After two weeks of incubation, 212VRT medium was aspirated from the lower chamber using a vacuum pump and replaced with 20 mL of 212RT (no silver nitrate) medium. Calli were immersed for one minute once every 24 hours for two more weeks. After completing 4 weeks of selection phase, selection medium was replaced with BAP-pulse medium 217A (N6 basal salts with 1 mg/L Thiamine HCL, 1 mg/L Nicotinic Acid, 3.52 mg/L BAP, 0.91 g/L L-Asparagine Monohydrate, 0.1 g/L myo-inositol, 0.5 g/L MES, 1.6 g/L $MgCl_2.6H_2O$, 0.1 g/L casein hydrolysate, 0.69 g/L Proline, 20 g/L sucrose, 250 mg/L Carbenicillin). Calli were treated with 217A medium for 7 days with one minute of immersion once every 12 hours.

For plant regeneration, 217A medium was replaced with 632AG medium (MS salts mixture, MS vitamins, 50 mg/L myo-inositol, sucrose 60 g/L, paromomycin 50 mg/L and carbenicillin 250 mg/L). Medium was injected into the upper chamber of TIS and two quick runs of one minute of immersion were performed to dilute out any residual 217A medium. Lights in the Percival were turned on to a 16 h on/8 h off cycle. TIS was left idle (without any immersion) for 72 hours and thereafter calli were immersed once every 24 hours till shoots developed to the size of 5-20 mm.

After 10-12 weeks of selection and regeneration in one vessel, transgenic plants were obtained. A transformation frequency of 5.9% was achieved in the TIS. This compares to 17.7% in the control.

Example 3

Use of Petri Plates

The calli obtained as in Example 1 were washed with 212V liquid medium containing 0.1 mM $AgNO_3$ and transferred to either a 25×100 mm Petri plate containing filter paper or large shallow Petri-plate (240×240 mm) containing two layers of (220×220 mm) acrylic felt.

Explants were then cultured as described in the TIS in Example 2 with the difference being that the liquid media exchanges were done by hand. The liquid media was compared with gelled media. In the smaller Petri plate, liquid media gave a transformation frequency of 4.2% compared to 6.6% with gelled media. In the larger Petri plate, liquid media gave a transformation frequency of 7.8% compared to 11.5% with gelled media. This demonstrates that liquid media is a viable alternative to the standard solid media protocols. Liquid media will allow for greater automation.

Example 4

Use of Multiple-Well Plates as Container

Multi-well plates can also be used as the single container system. Experiments were done as described above except for the use of multi-well plates instead of Petri plates. Multi-well plates from Costar (Corning Life Sciences, Acton, Mass.) were used with or without their Transwell™ inserts. The size of the membrane pores used (0.10 allows the media to seep across the membrane to the corn tissue as needed, without flooding the tissue. Pipette tip access ports allow media to be quickly removed and added into the wells for media changes. During media transfers, the media within the wells is changed by aspirating out the old media with a vacuum hose and pipetting in new media.

The multi-well plates used in this invention come in a size of 24 separate wells (with inserts) per plate. Alternatively, multi-well plates with a common, as opposed to separate, media reservoir can be used. The plates are typically wrapped with Nescofilm® or Parafilm™, or left unwrapped and stored in incubators (27° C.) in the same manner that is done with solid medium selection. The fact that the wells are separated from each other is particularly beneficial because bacterial contamination does not spread to other explants, as could be the case in common medium reservoirs, felt liquid selection, or solid medium selection.

The vector pMON 68410 was used for transformation and contained the nptII gene as a selectable marker and gfp as a scorable marker. Callus tissue of LH244 was used as an explant. Transformation steps were the same as disclosed in Example 8. Experiments were also done in the Costar multi-well plates with and without different matrices for providing support to the explant in liquid medium. Glass beads, silicon beads, felt, foam, and solid media with additional liquid medium were used. Control treatments were: culture on solid medium in Petri plates (trt #1; Table 1) and only liquid medium in multi-well plates (trt #2; Table 1). The different matrices were used in four experiments by four different people. All treatments yielded transgenic plants. However, use of silicon bead matrix and the small felts were at par with the control treatment of culture on solid medium in Petri plates.

TABLE 1

Use of multi-well plates with and without matrices for producing transgenic corn plants from callus explants.

| Trt # | Matrix/ Medium | # of callus pieces for each experiment | % TF Exp. 1 | Exp. 2 | Exp. 3 | Exp. 4 | Total |
|---|---|---|---|---|---|---|---|
| 1 | Gel/solid in Petri Plate | 48 | 39.6 | 50.0 | 50.0 | 25.0 | 41.1 |
| 2 | None/Liquid | 24 | 4.2 | 25.0 | 16.7 | 8.3 | 13.5 |
| 3 | Glass Beads/liquid | 24 | 25.0 | 12.5 | 33.3 | 16.7 | 21.9 |
| 4 | Silicon Beads/ liquid | 24 | 33.3 | 25.0 | 29.2 | 50.0 | 34.4 |
| 5 | Small Felt/ liquid | 24 | 41.7 | 25.0 | 54.2 | 29.2 | 37.5 |
| 6 | Foam | 24 | 0.0 | 16.7 | 0.0 | 4.2 | 5.2 |
| 7 | Solid medium with additional liquid medium | 24 | 16.7 | 16.7 | 12.5 | 4.2 | 12.5 |

Table 2 shows that multiple-well system with (trt#3 to 5) and without (trt#6) matrices can also be used for producing transgenic corn plants utilizing immature embryos as explants and glyphosate as a selective agent. The vector pMON 92690 for this study contained cp4 and gus genes. Transfer of media in multi-wells was done on a weekly basis.

TABLE 2

Use of multi-well plates with and without matrices for producing transgenic corn plants from embryo explants.

| Trt # | Container | Medium | Matrix | # of embryos | % TF |
|---|---|---|---|---|---|
| 1 | Petri plate | Solid | Gel | 40 | 60.0% |
| 2 | Petri plate | Liquid | Felts | 40 | 45.0% |
| 3 | Multi-well | Liquid | Silicon Beads | 40 | 25.0% |
| 4 | Multi-well | Liquid | Glass Beads | 40 | 15.0% |
| 5 | Multi-well | Liquid | Small Felt | 40 | 37.5% |
| 6 | Multi-well | Liquid | None | 48 | 2.1% |

Example 5

Use of a Single Petri Dish with Solid Medium Followed by Liquid Medium

Another example of a single-container system is the use of a single Petri dish with solid medium and subsequently adding liquid medium to facilitate selection and regeneration in the single plate without replacing the old medium. Corn callus was obtained and inoculated as described in Example 7.

Callus was then co-cultured in a 25×100 deep Petri-dish containing one Whatman filter paper and 100 μL of ½ MSPL medium at 23° C. After 3 days, the callus was transferred to solid medium 850QRT (4.33 g/L MS salts, 0.5 mg/L thiamine HCl, 0.5 mg/L pyridoxine HCl, 0.5 mg/L nicotinic acid, 100 mg/L myo-inositol, 0.5 g/L casein hydrolysate, 1.38 g/L proline, 30 g/L sucrose, 0.5 mg/L 2,4-D, 10 μg/L BAP, 20 μM AgNO3, 500 mg/L carbenicillin, 100 mg/L paromomycin, pH 5.8, 6 g/L agar).

After 14 days, 7-10 mL of fresh 850QRTT medium (850QRT without the agar and with 200 mg/L paromomycin) was added and plates were incubated in low light. After an additional 14 days, 7-10 mL of fresh 850RT medium (4.33 g/L MS salts, 0.5 mg/L thiamine HCl, 0.5 mg/L pyridoxine HCl, 0.5 mg/L nicotinic acid, 100 mg/L myo-inositol, 0.5 g/L casein hydrolysate, 1.38 g/L proline, 30 g/L sucrose, 0.5 mg/L, 10 μg/L BAP, 500 mg/L carbenicillin, 100 mg/L paromomycin, pH 5.8) was added and plates were further incubated in low light.

After another 14 days, the regenerated shoots were transferred to 632AT medium (4.33 g/L MS salts, 0.5 mg/L thiamine HCl, 0.5 mg/L pyridoxine HCl, 0.5 mg/L nicotinic acid, 50 mg/L myo-inositol, 60 g/L sucrose, 250 mg/L carbenicillin, 100 mg/L paromomycin, pH 5.8, 6 g/L agar). Regenerated plants were then transferred to phytatrays containing the same medium after 14 days, and then transferred to soil in 2 weeks.

Plants selected and regenerated in solid media produced about 46% usable transformed plants compared to 47% usable transformed plants from the control method using liquid medium on a felt support.

Example 6

*Agrobacterium*-Mediated Transformation of Maize Using a Novel Suspension Culture Method It is known in the art that the generation of transformable cell suspension culture is time consuming and often results in generation of non-embryogenic cells. This example describes a highly reproducible method (referred to here as "short suspension culture" or "SSC") for producing a rapid suspension culture that is highly embryogenic and very competent for *Agrobacterium*-mediated gene transformation. SSC as an explant combines the desirable characteristics of callus (embryogenic and easy to use), and of suspension cultures (uniform, highly regenerable, and amendable to high throughput production). In this non-limiting example, neomycin phosphotransferase II (nptII) was employed as a selectable marker and a standard binary vector system was used for efficient selection and regeneration of *Agrobacterium*-mediated stable transgenic events in maize.

*Agrobacterium* Strain, Plasmid, and Culture.

Disarmed *Agrobacterium tumefaciens* EHA 101 harboring the binary vector pMON25457 was used in this experiment. pMON25457 contained selectable (nptII) and reporter (uidA) genes, each driven by an enhanced 35S promoter ("e35S") and followed by an untranslated hsp70 intron. The uidA gene has an additional intron within its coding sequence to minimize bacterial expression. Plasmids were introduced into the *Agrobacterium* strain by electroporation with a Bio-Rad Gene Pulser operated at 2.5 kV and 400 Ohms. Transformed colonies were selected on solid Luria-Bertani (LB) medium (Sambrook and Russell, 2001) containing 100 mg/L each of kanamycin and gentamycin.

Induction and Growth of *Agrobacterium*.

*Agrobacterium* cells used for transformation were pre-induced with acetosyringone (200 μM) and glucose (2%) in AB-based induction medium (0.1 M MES, 0.5 mM $NaH_2PO_4$, 2% glucose, 1 g/L $NH_4Cl$, 300 mg/L $MgSO_4.7H_2O$, 150 mg/L KCl, 10 mg/L anhydrous $CaCl_2$, 2.5 mg/L $FeSO_4.7H_2O$, pH adjusted to 5.4 with NaOH).

A general procedure for inducing *Agrobacterium* cells follows. A loopful of bacterial colonies was picked from a fresh plate and grown at 28° C. in 50 mL LB medium containing appropriate antibiotics. The optical density at 660 nm of the bacterial culture after about 15 to 24 hours culturing was about 1.4. A 10-mL aliquot of the culture was transferred into 50 mL fresh LB medium containing appropriate antibiotics and grown for an additional 6 to 8 hours to an optical density at 660 nm of about 1.2. The *Agrobacterium* cells were centrifuged at 4° C. for 10 min at 3250×g. The resulting pellet was resuspended in the induction medium to a final optical density at 660 nm of about 0.2 and incubated at 28° C. for about 12 to 15 hours. Prior to use for transformation, the *Agrobacterium* cells were centrifuged at 4° C. for 10 min at 3250×g. After decanting the supernatant, the pellet was resuspended in ½ MSVI medium (2.2 g/L MS salt (Gibco), 1 mL/L of 1000× stock MS vitamins, 115 mg/L proline, 10 g/L glucose, 20 g/L sucrose, pH 5.4, filter-sterilized) and supplemented with 200 μM acetosyringone. At least 100 mL of ½ MS VI medium supplemented with 200 μM acetosyringone was used for every 1 L *Agrobacterium* suspension. The resuspended cells were aliquoted into smaller volumes, centrifuged at 4 degrees C. for 10 min at 3250×g, the supernatant discarded and the pellets stored in ice until use (up to 4 hours). Pellets were resuspended to a desired optical density with ½ MS VI medium supplemented with 200 μM acetosyringone, with a suspension of about 109 cells/mL giving an optical density at 660 nm of about 0.2.

Growth of Stock Plants and Callus Formation.

Maize Hi-II and FBLL genotypes were grown in the greenhouse at 16-h day length. Crosses involving these two genotypes were made and immature embryos were excised onto a modified N6 medium (Chu et al., 1976) supplemented with 1.0 mg/L 2,4-D,1 mg/L thiamine HCl, 0.5 mg/L nicotinic acid, 0.91 g/L L-asparagine monohydrate, 100 mg/L myo-inositol, 0.5 g/L MES, 1.6 g/L $MgCl_2.6H_2O$, 100 mg/L casein hydrolysate, 0.69 g/L proline, and 20 g/L sucrose; the modified N6 medium was solidified with 2 g/L Gelgro (catalogue number 150180, ICN Biomedicals) and medium pH was adjusted to pH 5.8 with KOH (pre-autoclave). The same growth conditions were used for the elite genotype RBDQ2. The FBLL×Hi-II hybrid and RBDQ2 callus lines were subcultured at 2-week intervals and maintained at 28° C. in the dark for up to four months on the same medium. This subculture protocol also worked with the Hi-II and FBLL-MAB lines.

Short Suspension Culture (SSC) Formation.

A general protocol for generating SSC from calli follows. To initiate SSC formation, about 2 g of calli, 2 weeks post sub-culture, were transferred to a 250-mL baffled flask containing 80 mL MS Fromm medium supplemented with 2.0 mg/L 2,4-D, 20 g/L sucrose, 150 mg/L L-asparagine, 100 mg/L myo-inositol, 1 mL MS Fromm 1000× vitamin stock containing 650 mg/L nicotinic acid, 125 mg/L pyridoxine HCl, 125 mg/L thiamine HCl, and 125 mg/L calcium pantothenate (medium pH adjusted to 5.8 with KOH). The SSC were generated on a gyratory shaker set to 170 rpm and 28 degrees C. During each subsequent transfer, tissues were allowed to briefly settle to the bottom of the flasks in order to remove undesirable cell types (for example, cells that were elongated, thick-walled, low in cytoplasmic content, or non-dividing), before the suspension was transferred with a wide-mouth Falcon™ sterile disposable pipette. On day 1 post initiation, the tissue from the flask were transferred to a fresh flask containing 80 mL modified MS medium and grown for two more days; this transfer step was repeated at day 3 post initiation. On day 5 post initiation, the tissue was equally divided between two flasks, giving about 2.5 mL packed cell volume (PCV) per flask. Thereafter, the medium was replaced every 3 days. By day 14 post initiation, the resulting packed cell volume in each flask was about 6 mL (approximately 4 g per flask, or about a four-fold increase in total PCV over 2 weeks). These cells ("SSC") were transferred to fresh medium on day 14 post initiation, and transformation was initiated on day 15 post initiation. The relatively frequent change of medium throughout this SSC procedure permitted rapid tissue proliferation. An additional advantage of the SSC procedure was that no visual selection of tissues was required at each transfer step, making this system both practical and reproducible.

Inoculation and Co-Culture.

Three flasks containing a combined total of about 18 mL PCV were used in a transformation study of FBLL×Hi-II hybrid SSC explants. Pilot experiments were conducted to enhance parameters involved in the various transformation steps. A modified co-culture technique was used as described by Cheng et al. (2003), which is incorporated by reference herein. A desiccation step was employed post *Agrobacterium* infection, which was found to greatly increase T-DNA transfer as well as to increase recovery of transgenic events.

FBLL×Hi-II hybrid SSC tissue from each flask along with some liquid medium was equally divided and transferred to two wells of a six-well tissue culture dish (Corning CoStar™, non-treated, part number 9088), or, alternatively, to a 20×60 mm Petri dish The liquid medium was removed from each well or dish. Five mL of *Agrobacterium* suspension (OD660 nm~0.5) in ½ MS VI medium supplemented with 200 μM acetosyringone was added to each well or dish, followed by a 1-h inoculation period. At the end of the inoculation period, most of the *Agrobacterium* suspension was gently removed and the inoculated SSC cells washed with 5 mL ½ MS VI medium supplemented with 200 μM acetosyringone. Cells from each well or dish were transferred to a Petri dish containing 3 layers of sterile filter paper to absorb excess liquid from the cells, and then divided equally and transferred to two 60×20 mm Petri dishes, each containing a piece of 5.5 cm diameter sterile filter paper (Baxter). A total of 12 filter paper-containing co-culture dishes were thus obtained (4 from each original flask). The transferred cells were arranged in 6 to 8 clumps on the filter paper. One day co-cultivation under desiccation was performed using a modified protocol of Cheng et al. (2003), which is herein incorporated by reference in its entirety. One hundred µL ½ MS VI medium supplemented with 200 µM acetosyringone was added to each filter paper, and the plates were wrapped with Parafilm™ and incubated in the dark at 23 degrees C. Transformation frequency was calculated as number of independent events regenerated per mL PCV.

Transformation experiments were similarly conducted with RBDQ2 SSC explants, using three replicate packed cell volumes (4.5 mL each). The transformation procedure was generally the same as that used with the FBLL×Hi-II hybrid SSC explants, except that, for one of the two wells per flask, ½ MS VI medium supplemented with 200 µM acetosyringone and containing 20 µM $AgNO_3$ was used during the inoculation and wash steps.

Selection and Regeneration of Transgenic Plants.

The protocol for transformation of SSC with nptII using paromomycin selection involved a simple filter paper support for transfer of explants during selection, which minimized labor, ensured rapid elimination of *Agrobacterium*, increased growth rate of the tissue, and resulted in faster selection.

This procedure was performed on FBLL×Hi-II hybrid SSC as follows. On day 0 of transformation (that is at the end of the co-culture step), a washing step was carried out with 5 mL MS Fromm medium supplemented with 1000 mg/L carbenicillin, 100 mg/L ticarcillin, 100 mg/L vancomycin, and 40 mM $AgNO_3$ that was added directly to each of the co-culture plates, and cell clumps gently tapped using a sterile spatula to ensure submersion. The wash medium was removed from the plates, and the filter papers carrying the cells were transferred to Petri dishes containing fresh solid Duncan "D" medium containing 3.0 mg/L 2,4-D supplemented with 1000 mg/L carbenicillin, 100 mg/L ticarcillin, and 40 micromolar $AgNO_3$ as a delay medium. Duncan "D" medium contains basal salts and vitamins of the "D" medium as described by Duncan et al. (1985), which is incorporated by reference herein; generally 500 mL of a 2× stock of this medium was prepared and added to 500 mL of autoclaved sterile distilled water containing 6 g of Phytagar. Cells were maintained in delay medium for 6 days. On day 6 of transformation, a first selection step was performed with the filter papers carrying the cells transferred to Petri dishes containing Duncan "D" medium with 1.5 mg/L 2,4-D supplemented with 750 mg/L carbenicillin, 100 mg/L ticarcillin, 40 micromolar $AgNO_3$, and 50 mg/L paromomycin as a first selection medium. Two weeks after the end of the co-culture step, a second selection step was performed with the filter papers carrying the cells transferred to Petri dishes containing Duncan "D" medium with 1.5 mg/L 2,4-D supplemented with 750 mg/L carbenicillin, 100 mg/L ticarcillin, 40 micromolar $AgNO_3$, and 100 mg/L paromomycin as a second selection medium. Three weeks after the end of the co-culture step, a third selection step was performed with pea-sized clumps of tissue removed from each filter paper and plated onto a solid Duncan "D" medium with 1.5 mg/L 2,4-D supplemented with 750 mg/L carbenicillin, 100 mg/L ticarcillin, and 100 mg/L paromomycin as a third selection medium. There were about 4 to 6 resulting clumps of cells plated from each filter paper, and each cell clump was treated individually henceforth in the experiments. One plated clump per filter paper was histochemically assayed for transgenic sector size, which was found to be about 1 to 2 mm in diameter. Four weeks after the end of the co-culture step, a fourth selection step was performed with each clump transferred to Petri dishes containing Duncan "D" medium supplemented with 1.5 mg/L 2,4-D supplemented with 750 mg/L carbenicillin, 100 mg/L ticarcillin, and 100 mg/L paromomycin. At the end of this fourth selection cycle, a total of 232 paromomycin-resistant FBLL× Hi-II hybrid lines were obtained. Seven weeks after the end of the co-culture step, a selection and pre-regeneration step is was carried out with the resistant calli transferred to deep Petri dishes (20×100 mm) containing 3.52 mg/L 6-BAP, 500 mg/L carbenicillin, and 100 mg/L paromomycin for one week. Finally, regenerating tissues were transferred to an MS regeneration medium for two weeks in Petri dishes, followed by transfer to a Phytatray for an additional three weeks. MS regeneration medium consisted of modified MS medium supplemented with 10 g/L glucose, 20 g/L sucrose, 100 mg/L myo-inositol, 150 mg/L L-asparagine, and 1 mL/L MS Fromm 1000× vitamin stock containing 650 mg/L nicotinic acid, 125 mg/L pyridoxine HCl, 125 mg/L thiamine HCl, and 125 mg/L calcium pantothenate, and 6 g/L Phytagar; medium pH was adjusted to 5.8 with KOH pre-autoclave, and 250 mg/L carbenicillin and 100 mg/L paromomycin were added post-autoclave. Thirteen weeks after the end of the co-culture step, the resulting plantlets were transferred to soil.

Progeny Analysis of Transgenic Plants.

UidA activity was assayed at various stages of selection and transformation, following the histochemical procedure described by Jefferson (1987), which is incorporated by reference herein, at various stages of transformation and plant growth. Detection and copy number analysis of nptII was performed with INVADER® assays (Third Wave Technologies, Madison, Wis.). At least under the experimental conditions described above, a delay step followed by a step-wise increase in selection pressure was found to be necessary to recover transgenic sectors from SSC explants. In general, *Agrobacterium*-mediated transformation competence of maize cells was found to be improved by subjecting callus to at least a short liquid phase prior to initiating transformation. For example, FBLL×Hi-II hybrid SSC explants were found to be highly competent to T-DNA transfer between about 5 days to about 14 days post initiation of SSC with 80% of the tissues expressing gus at 3 days post transformation. Older (2 month) SSC cultures were also found to be competent to transformation, with about 20% of the explants exhibiting histochemical staining for uidA activity 3 days post transformation. In contrast, FBLL×Hi-II hybrid calli maintained on 211 modified N6 medium were found to be poorly competent, with less than 20% of the explants exhibiting histochemical staining for UidA activity 3 days post transformation.

In the case of the FBLL×Hi-II hybrid genotype, a total of 232 paromomycin-resistant lines were obtained from the original three flasks. Of 76 resistant callus lines tested, 56 (about 74%) were found to express uidA. A sub-set of 35 paromomycin-resistant lines were regenerated; of these, 24 of 25 events that were regenerated into plants were found to contain uidA. Southern blots and histochemical assays of plants arising out of several SSC experiments confirmed integration of the transgene in the R1 generation, and inheritance of the transgenes by R0 and R1 generations. In the case of the RBDQ2 genotype, 3 replicate flasks (each containing about 4 mL PCV) yielded a total of 37 paromomycin-resistant, uidA-positive putative events. Transformation frequency was underestimated because some tissues were sacrificed for UidA histochemical assays. In this genotype, use of AgNO₃ during inoculation or washing did not enhance transformation frequency, suggesting that suppression of *Agrobacterium* growth by desiccation was sufficient to minimize *Agrobacterium* toxicity. A total of 29 putative paromomycin-resistant calli were generated, out of which 18 putative events were transferred to soil. Seventeen of the 18 events were found to be uidA-positive by histochemical assays of leaf tissue. Thus, transformation frequency of RBDQ2 SSC (based on the putative events) was estimated to be approximately 1.4 event/1 ml PCV (17 events/12 mL PCV).

This SSC procedure was thus capable of rapidly establishing regenerable type II suspension cultures, suitable for *Agrobacterium*-mediated stable transformation, from both the FBLL×Hi-II hybrid and the proprietary elite RBDQ2 genotypes. SSC explants may be especially useful in the development of a high-throughput gene evaluation system.

Example 7

Preparation of *Agrobacterium* for Transformation by Direct Inoculation of a Frozen Glycerol Stock of *Agrobacterium* into an Induction Medium This is a non-limiting example of one method of preparing *Agrobacterium* for transformation. More specifically, this example describes direct inoculation of a frozen glycerol stock of *Agrobacterium* into a vir induction broth.

The transfer of T-DNA into plant cells using the Ti plasmid requires activation of the vir genes encoding the proteins VirA and VirG. The signals for VirA activation include, for example, acidic pH, phenolic compounds (for example, acetosyringone), and certain sugars that act synergistically with phenolic compounds. Conventionally, pre-induction of vir genes involve growing *Agrobacterium* cells (usually from a frozen stock) in a growth medium for a varying period of time, measuring *Agrobacterium* density, adjusting to a desired density, growing in AB minimal induction medium or other suitable medium for induction, spinning and washing the cells, and finally adjusting the *Agrobacterium* culture to a desired density prior to inoculation. The numerous steps involved require considerable time and effort, and provide opportunities for undesired variability in experiments.

Disclosed here is a rapid, single-step *Agrobacterium* direct induction procedure that reduces time, effort, and variability in transformation experiments. The reduction in number of steps required for induction is also advantageous for quality control purposes and reduction of ergonomic burden.

In the non-limiting embodiments described herein, the vector pMON 70801 carrying a gene (cp4) for glyphosate resistance (see U.S. Pat. No. 5,633,435, which is incorporated by reference in its entirety herein) was used; however, many other *Agrobacterium* vectors could be used, as is known in the art. Optical densities (OD) were measured at 660 nanometers. Additional suitable procedures, including descriptions of media and reagents, for transformation of plants using glyphosate selection, have been disclosed, for example, in U.S. Patent Appln. Publn. 2004/0244075 to Cai et al., which is incorporated by reference in its entirety herein.

Direct Induction with Modified MS Induction Medium.

In a non-limiting embodiment, the procedure can involve pre-induction of a frozen *Agrobacterium* glycerol stock in an MS induction medium containing necessary vir induction components. After pre-induction, the *Agrobacterium* cells are used directly in transformation experiments.

*Agrobacterium* was grown from a frozen stock made with MS medium (½MS salts, 100 µM MES, 2% glucose with 25% (v/v) glycerol). The frozen stock made with MS salts was resuspended in a modified MS induction broth containing acetosyringone (½MS salts, 100 µM MES, 2% glucose supplemented with appropriate antibiotics (Spec/Strep 50 µg/milliliter, Kanamycin 50 µg/milliliter, and Chloramphenicol 25 micrograms/milliliter, and 200 µM acetosyringone). A total of 5 hours induction was followed with an initial OD of 0.4. For induction, one flask (250-mL baffled flask) with 50 milliliters of induction medium was used. At the end of the induction *Agrobacterium* suspension was used directly for inoculation and was supplemented with 20 µM AgNO₃ just prior to inoculation.

The above-described modified MS direct induction protocol was compared with a conventional protocol involving the following steps: *Agrobacterium* was grown from a frozen stock for 8 hours in LB liquid with appropriate antibiotics (Spec/Strep 100 micrograms/milliliter, kanamycin 100 micrograms/milliliter, and chloramphenicol 25 micrograms/milliliter). *Agrobacterium* was spun down and resuspended in an AB minimal induction broth with appropriate antibiotics (spec/Strep 50 micrograms/milliliter, kanamycin 50 micrograms/milliliter, and chloramphenicol 25 micrograms/milliliter), and 200 micromolar acetosyringone. A total of 13 hours induction was followed with an initial OD of 0.2. For induction one flask (1-liter baffled flask) containing 300 milliliters of induction medium was used. At the end of induction *Agrobacterium* was spun down and resuspended with ½MSVI supplemented with 200 micromolar acetosyringone to an OD of 0.4. AgNO₃ was added to a final concentration of 20 micromolar just prior to inoculation.

Explants for this study were calli derived from a near-elite corn line sub-cultured on fresh medium 8 days prior to initiating transformation on N6-based 201 medium. Inoculation was performed in 25×100 millimeter deep dishes. About 6 grams of calli were transferred to a deep dish containing 50 milliliters of ½ MS VI (one dish per treatment). Explants were washed and all liquid was removed. Twenty milliliters of *Agrobacterium* suspension (OD 0.4) supplemented with acetosyringone (final concentration 200 micromolar) and AgNO₃ (final concentration of 20 micromolar), and a 1 hour inoculation was performed. *Agrobacterium* suspension was removed after inoculation and the explants were washed with 15 milliliters ½ MSVI supplemented to concentration of 20 micromolar AgNO₃ and 200 micromolar acetosyringone. Calli from each inoculation dish were transferred to a deep dish containing 10 filter papers (7.5 millimeters; Baxter catalogue number 28313-046) to remove the excess liquid. About 0.5 is gram (wet weight) or about 2.5 grams (drained weight) of callus was transferred to a single co-culture plate (25×60 millimeters) containing a single filter paper (5.5 millimeters; Baxter catalogue number 28297-868). Explants were arranged in four groups towards the edge of the co-culture plate. Co-culture was performed with or without desiccation (1 milliliter of ½ MSVI was added) at 23° C. for 18 hours. For each treatment, that is conventional induction or modified MS induction, seven replicates (4 without desiccation, 3 with desiccation) were used. No statistically significant difference was observed between the two induction protocols. The modified MS direct induction protocol was shown to produce about the same number of putative events as did the lengthier conventional protocol.

Direct Induction with AB Induction Medium.

In another non-limiting embodiment, the procedure involved pre-induction of a frozen *Agrobacterium* glycerol stock in an AB induction medium containing necessary vir induction components. After pre-induction, the *Agrobacterium* cells were adjusted to the desired density and used directly in transformation experiments. *Agrobacterium* was grown from a regular LB frozen stock with an *Agrobacterium* optical density (OD) of 3.0 measured at 660 nanometers (final concentration).

An *Agrobacterium* culture was prepared and split into two portions. One portion was grown for an additional 4.5 hours to OD ~0.6 in 36 milliliters of 2XYT medium, centrifuged, resuspended at OD ~3.0 in AB minimal medium containing 20% glycerol, and frozen for use in a direct induction protocol. For induction, 5 milliliters of the frozen stock was thawed, added to 70 milliliters AB minimal medium containing acetosyringone, and induced overnight.

The second *Agrobacterium* culture portion was streaked onto plates and incubated 3 days; a first seed culture prepared from these plates was grown overnight. This was followed by a second seed culture prepared from the first seed culture, grown for a day and induced overnight at OD ~0.2 in AB minimal medium containing acetosyringone.

The two induced *Agrobacterium* preparations were used to inoculate maize embryos in parallel experiments. Maize embryos from half of each ear were excised into each of the *Agrobacterium* preparations (OD ~1.0) for 15 minutes, and then allowed to sit for 5 minutes. The embryos were removed and placed onto co-culture plates. Using the is conventional protocol, a total of 883 embryos were inoculated, resulting in a total of 174 (20%) plants to soil and an average transformation frequency of 17% (standard deviation=11.4). Using the direct induction protocol, a total of 814 embryos were inoculated, resulting in a total of 153 (19%) plants to soil and an average transformation frequency of 19% (standard deviation=11.6). Copy number of the cp4 transgene was found to be similar between treatments.

Example 8

Methods for Preparing Corn Callus for Sub-Culturing by Mechanical Means

One of the greatest ergonomic burden and time-consuming processes of a corn transformation production system is the establishment and maintenance of embryogenic callus for *Agrobacterium* mediated transformation which requires manual breaking of callus during the sub-culturing step. Furthermore, during the transformation process, many cells are transformed in a single immature embryo or a single piece of callus. However, current selection and regeneration practices treat each population of transformed cells in a single immature embryo or piece of callus as a single event, regenerating usually one plant per piece of tissue.

In order to relieve the ergonomic burden created by manual pinching by forceps of callus, especially type I callus, several mechanical means such as coffee grinders, baby food mills, peppercorn grinders, herb grinders, garlic cutters, and garnish knives were tested as a means for breaking or cutting callus for sub-culturing. Among these means, herb grinder and garnish knife were found to be most suitable for breaking or cutting callus and in producing callus pieces suitable for subculture and transformation.

Use of mechanical means for preparing corn callus for sub-culturing can also be used to separate many transformed cells within a given unit of tissue by cutting or breaking up the tissue into smaller units of individually transformed cells from which a transformed plant may be regenerated thus obtaining more transgenic plants from the same unit of tissue.

The callus for this example was derived by culturing immature corn embryos on is callus medium 1074 (Table 3), that were isolated from developing kernels about 10 days after pollination. Five to nine week old callus was treated with an herb grinder and contacted with *Agrobacterium* containing a vector carrying nptII gene for selection for up to 60 minutes. The inoculated callus was blot dried and co-culture/desiccated for 2-3 days at 23° C. in dark. The callus tissue was then transferred to felt pieces in liquid selection medium 1086 (Table 3) containing about 50 mg/L of paromomycin and cultured for up to 30 days at 27-28° C. in dark to select for the transformed tissue containing the nptII selectable marker gene. The transformed tissue was then regenerated into plants by culturing the tissue surviving selection in shooting medium 1087 (Table 3) containing BAP to induce shoots for 5-7 days at 27-28° C. in 16-h light. The growing tissue was incubated in medium 1067 (Table 3) for further 2-3 weeks to induce roots. Healthy shoots with or without roots were transferred to Phytatrays containing medium 1067 and subsequently to soil for growing.

TABLE 3

Media compositions used.

| Media Components/ L (Supplier) | 1074 | 1086 | 1087 | 1067 |
|---|---|---|---|---|
| MS Basal Salts (Phytotech) | 4.33 g | 4.33 g | 4.33 g | 4.33 |
| MS Vitamins (100X) (Phytotech) | 10 mL | 10 mL | 0 | 0 |
| MS Fromm Vitamins (1000X)* | 0 | 0 | 1 mL | 1 mL |
| BAP (Sigma) | 0 | 0 | 3.5 mg | 0 |
| Thiamine HCL (Sigma) | 0.5 mg | 0.5 mg | 0 | 0 |
| 2,4-D (Phytotech) | 0.5 mg | 0.5 mg | 0 | 0 |
| Sucrose (Phytotech) | 30 g | 30 g | 30 g | 0 |
| Glucose (Phytotech) | 0 | 0 | 0 | 10 g |
| Maltose (Phytotech) | 0 | 0 | 0 | 20 g |
| Proline (Sigma) | 1.38 g | 1.38 g | 1.38 g | 0 |
| Casamino Acids (Difco) | 0.5 g | 0.5 g | 0.5 g | 0 |
| Asparagine monohydrate (Sigma) | 0 | 0 | 0 | 0.15 g |
| Myo-inositol (Sigma) | 0 | 0 | 0 | 0.1 g |
| Phytagel (Sigma) | 3 g | 0 | 3 g | 0 |
| Phytagar (Gibco) | 0 | 0 | 0 | 6 g |
| Carbenicillin (Phytotech) | 0 | 500 mg | 250 mg | 250 mg |
| Picloram (Sigma) | 2.2 mg | 2.2 mg | 0 | 0 |
| Paromomycin (Phytotech) | 0 | 100 mg | 100 mg | 100 mg |
| Silver Nitrate (Sigma) | 3.4 mg | 3.4 mg | 0 | 0 |
| pH | 5.8 | 5.8 | 5.8 | 5.8 | comprising 1250 mg/L nicotinic acid (Sigma), 250 mg/L pyridoxine HCl (Sigma), 250 mg/L thiamine HCl (Sigma), and 250 mg/L calcium pantothenate (Sigma).

The results indicate that the herb grinder can be successfully used to break callus into pieces suitable for sub-culturing and transformation (Table 4).

TABLE 4

Use of herb grinder for breaking callus pieces for sub-culturing and transformation.

| Expt | Treatment & Description | Grams of callus used | No. of callus pieces put to selection | No. of plants produced | TF (%) |
|---|---|---|---|---|---|
| 1 | 1. Hand excised, hand subcultured | 2.5 | 192 | 53 | 27.6 |
| | 2. Hand excised, mechanical subcultured | 2.5 | 185 | 39 | 21.1 |

TABLE 4-continued

Use of herb grinder for breaking callus pieces
for sub-culturing and transformation.

| Expt | Treatment & Description | Grams of callus used | No. of callus pieces put to selection | No. of plants produced | TF (%) |
|---|---|---|---|---|---|
| 2 | 1. Hand excised, hand subcultured | 1.5 | 144 | 9 | 6.3 |
|  | 2. Hand excised, mechanical subcultured | 1.5 | 116 | 17 | 14.7 |

A garnish knife (Pickle Slicer, #4428 from International Culinary, Mystic, Conn.) was also used a means for cutting callus for reducing the ergonomic burden of hand-subculture methods. The garnish knife consisted of 8 parallel blades attached to the end of a plastic handle. The knife was sterilized with a mild bleach soak, followed by an ethanol soak, and then left to dry for approximately 30 minutes. While the knife was drying, 4-week old callus (hand-sub-cultured at 2 weeks) was placed in a 150×15 mm Petri dish, and divided into 3 to 4 smaller piles within the dish, each containing approximately 40-60 callus pieces. Working with one pile at a time, the knife was used to cut through the callus. With a sterile implement, the callus was pushed out of the knife that had collected between the blades onto the plate, where it was cut a second time. Other callus piles were treated the same way. The cut callus was used for sub-culturing and transformation.

Data from several garnish knife experiments showed a transformation frequency is of 13.16%. In additional tests, the transformation frequency of hand subcultured callus of 21.5% was comparable to callus prepared by garnish knife (18.9%). In yet another 74 experiments using garnish knife as a means for cutting callus by 5 different users, the average transformation frequencies across all users was 19.4% indicating utility of this method.

Example 9

Methods for Inoculating Explants with
Agrobacterium for Transformation

The current methods for *Agrobacterium*-mediated transformation, for example, of corn immature embryos uses many steps involving excising one embryo at a time from the kernels, incubating them in *Agrobacterium* cell suspension, removing *Agrobacterium* suspension, transferring the embryos to a co-culture plate for infection to occur, orienting the embryos and placing them with scutellum side up and finally transferring the embryos to a selection or delay medium for further manipulations such as selection and regeneration. Many of these steps are ergonomically unfriendly and also raise the possibility of damaging excised embryos and increased incidence of *Agrobacterium*-related cell death thereby resulting into reduced transformation frequency. Therefore, there is a need in the art of corn transformation to simplify inoculation step, such that it is ergonomically friendly and results in higher transformation frequency.

The inventors have now simplified the inoculation step by reducing the total number of steps by inoculating transformable explants, for example, immature embryo, by either 1) dipping a spatula in *Agrobacterium* suspension prior to excising the embryo with spatula; 2) by soaking the corn ear with *Agrobacterium* suspension before excising the embryo; or 3) by combing the two steps for example, by soaking the corn ear with the *Agrobacterium* suspension followed by excising the embryos by a spatula dipped in *Agrobacterium* suspension.

In general, the following transformation method was used. Immature corn embryos from a recipient corn line were dissected from developing kernels about 10 days after pollination and inoculated by either incubation, dipped spatula (18.0%), or soaking the ear with *Agrobacterium* containing the construct. The inoculated embryos were co-cultured on co-culture medium 1514 (Table 5) for about 24 hr at 23° C. in dark. The embryos were then transferred for selection onto selection medium 1278 (Table 5) containing 0.1 mM glyphosate to select for the transformed tissue containing the cp4 selectable marker gene and 500 mg/L Carbenicillin to inhibit *Agrobacterium* growth by incubating for 2-3 weeks at 27° C. in dark. The transformed corn tissue was then regenerated into plants by transferring transformed callus pieces onto the first regeneration medium 1073 (Table 5) and grown for 5-7 days with 16 hours light/8 hours dark photoperiod and 27° C. temperature. The tissue was then transferred onto the second regeneration medium 1071 (Table 5) for approximately 2 weeks. Regenerated shoots were transferred to rooting medium 1084 (Table 5) in Phytatrays. The developing plantlets were then transferred to soil, hardened off in a growth chamber at 27° C., 80% humidity, and low light intensity for approximately 1 week and then transferred to a greenhouse and grown under standard greenhouse conditions.

The *Agrobacterium* carrying plasmid pMON 92689 containing a modified CP4 aroA gene for glyphosate selection (U.S. Pat. No. 5,627,061) was grown for inoculation from a frozen stock made with MS induction medium as described in Example 7. The kernels on the cob were sterilized with 80% ethanol and cut at the crown and then washed with 100 ml of ½ MSVI and applied with 20 ml of *Agrobacterium* suspension. A spatula was dipped in *Agrobacterium* suspension and immature embryos were excised and plated on to the co-culture medium 1514 for 24 hrs at 23° C. in dark. These treatments were compared with a standard treatment wherein embryos were excised one at a time and incubated with *Agrobacterium* suspension for up to 5 min. The embryo size was 1.5-1.8 mm. However, the method was found to work well with other embryos sizes as well, for example, embryo sizes ranging from 1.4 to 2.2 mm. Transgenic events could be obtained by directly inoculating the explants with *Agrobacterium* while the explants were still attached to the maternal tissue and by inoculating explants while they were being removed from the source. Following transformation frequency were obtained for each treatment: inoculation by incubation (20.7%), inoculation by dipped spatula (18.0%), and inoculation by soaking the ear (17.0%).

Other means of contacting explants with *Agrobacterium* and duration of contact may be anticipated by those skilled in the art. For example, a knife dipped in *Agrobacterium* suspension can be used for inoculation by cutting leaf or callus tissue into smaller pieces or a dipped needle may be used to inoculate the plant tissue by inserting the needle into the plant tissue.

The method has been found to improve transformation frequency by allowing reduced tissue handling and reduced *Agrobacterium*-related cell death. With 6 different constructs, the dipped spatula method produced an average TF of 14.3% over standard incubation method which produced a TF of 9.2%.

TABLE 5

Media compositions used.

| Media Components/L (Suppliers) | 1233 | 1278 | 1514 | 1524 | 1073 | 1071 | 1084 |
|---|---|---|---|---|---|---|---|
| MS Basal Salts (Phytotech) | 2.165 g | 4.33 g | 4.33 g | 4.33 g | 4.33 g | 4.33 g | 2.165 g |
| MS Vitamins (100X) (Phytotech) | 10 mL | 10 mL | 10 mL | 10 mL | 0 | 0 | 0 |
| MS Fromm Vitamins (1000X)* | 0 | 0 | 0 | 0 | 1 mL | 1 mL | 0 |
| BAP (Sigma) | 0 | 0.01 mg | 0 | 0 | 3.5 mg | 0 | 0 |
| Thiamine HCL (Sigma) | 0.5 mg | 0.5 mg | 0.5 mg | 0.5 mg | 0 | 0 | 0 |
| 2,4-D (Phytotech) | 3 mg | 0.5 mg | 0.5 mg | 0.5 mg | 0 | 0 | 0 |
| NAA (Sigma) | 0 | 0 | 0 | 0 | 0 | 0 | 0.5 mg |
| IBA (Sigma) | 0 | 0 | 0 | 0 | 0 | 0 | 0.75 mg |
| Sucrose (Phytotech) | 20 g | 30 g | 30 g | 30 g | 30 g | 0 | 20 g |
| Glucose (Phytotech) | 10 g | 0 | 0 | 0 | 0 | 10 g | 0 |
| Maltose (Phytotech) | 0 | 0 | 0 | 0 | 0 | 20 g | 0 |
| Proline (Sigma) | 115 mg | 1.38 g | 1.38 g | 1.38 g | 1.38 g | 0 | 0 |
| Casamino Acids (Difco) | 0 | 0.5 g | 0.5 g | 0.5 g | 0.05 g | 0.5 | 0 |
| Asparagine monohydrate (Sigma) | 0 | 0 | 0 | 0 | 0 | 0.15 | 0 |
| Myo-inositol (Sigma) | 0 | 0 | 0 | 0 | 0 | 0.1 g | 0 |
| Low EEO Agarose (Sigma) | 5.5 g | 0 | 0 | 0 | 0 | 0 | 0 |
| Phytagel (Sigma) | 0 | 3 g | 3 g | 3 g | 3 g | 3 g | 3 g |
| Acetosyringone (Aldrich) | 200 uM | 0 | 0 | 0 | 0 | 0 | 0 |
| Carbenicillin (Phytotech) | 500 mg | 500 mg | 500 mg | 500 mg | 250 mg | 250 mg | 0 |
| Glyphosate (Gateway Chemical) | 0 | 0.1 mM | 0.1 mM | 0.1 mM | 0.1 mM | 0.1 mM | 0.1 mM |
| Silver Nitrate (Sigma) | 3.4 mg | 3.4 mg | 3.4 mg | 3.4 mg | 0 | 0 | 0 |
| pH | 5.2 | 5.8 | 5.8 | 5.8 | 5.8 | 5.8 | 5.8 |

*Comprising 1250 mg/L nicotinic acid (Sigma), 250 mg/L pyridoxine HCl (Sigma), 250 mg/L thiamine HCl (Sigma), and 250 mg/L calcium pantothenate (Sigma). For liquid media Phytagel was excluded from the composition.

Example 10

Agrobacterium-Mediated Transformation of Corn by Doing Inoculation, Co-Culture, and Selection in a Single Step Normally Agrobacterium-mediated transformation methods involve 3 distinct steps: inoculation of an explant with Agrobacterium, co-cultivation of inoculated explant on a medium absent of an antibiotic to allow for survival of Agrobacterium and to enhance infection of the explant, and selection of the transformed cell on a medium containing a selective agent such as kanamycin and glyphosate. There is always a need to reduce the number of steps required in a transformation method to improve production efficiencies. The inventors have now provided a method for Agrobacterium-mediated transformation of corn wherein inoculation, co-culture and selection steps can be combined into a single step by plating the inoculated explants directly onto a medium that contains selective agents for suppressing growth of Agrobacterium and killing non-transformed explant cells thereby allowing inoculation, co-culture, and selection in a is single step, thus improving transformation production system efficiencies.

In general the transformation method disclosed in Example 9 was used. The Agrobacterium containing pMON65375 containing a modified CP4 aroA gene for glyphosate selection (U.S. Pat. No. 5,627,061) for inoculation was prepared from a frozen stock made in AB minimal induction medium as disclosed in Example 7.

The spatula was dipped in Agrobacterium suspension prior to excising each embryo and excised embryos were plated onto co-culture medium 1233 and then on selection medium 1278 or plated directly onto the selection medium 1278. The results show that transformation can be done by combining inoculation, co-culture and selection in a single step with a variety of Agrobacterium concentrations and embryo sizes.

In another embodiment, transformation was also achieved by first culturing embryos on a selection medium and then applying Agrobacterium suspension immediately to the embryos rather than first applying Agrobacterium and then culturing embryos on the selection medium. Transgenic plants could also be obtained by applying additional Agrobacterium during co-culturing and selection.

Example 11

Selection of Transformed Cells on Sorbarods and Development of High-Throughput System Suitable explants such as callus and immature embryos can be obtained via mechanical and manual excision means known in the art and can be inoculated with Agrobacterium containing a plasmid comprising any gene of interest known in the art. In one embodiment, the selection of a transformed cell is done on a felt piece placed in the liquid medium and regeneration is done on Sorbarod™ plug (Baumgartner Papiers SA, Crissier-Lausanne, Switzerland) placed in the liquid medium. In another embodiment, both selection and regeneration of the transformed cell are done on a Sorbarod™ plug placed in the liquid medium.

The utility of these embodiments is demonstrated by several examples of data provided in Table 6. Compositions of media used are shown in Table 5 except for liquid media Phytagel was excluded. Immature corn embryos from the recipient line were dissected from developing kernels and inoculated with *Agrobacterium* containing binary vector pMON42073 comprising a CP4 gene for glyphosate selection. The inoculated embryos were co-cultured on co-culture medium 1514 (see Table 5 for composition) for about 24 hr at 23° C. in dark. The inoculated embryos were then transferred to either a 5×5 cm square felt piece (Consumer Products Enterprises (CPE) Inc., Union, S.C.) or a Sorbarod plug (ILA-CON Limited, Kent, UK) placed in the liquid selection medium 1278 (see Table 5 for composition) containing 0.1 mM glyphosate to select for the transformed tissue. After this step, used selection liquid medium 1278 was removed and replaced with the liquid first regeneration medium 1073 (see Table 5 for composition). The tissue was grown for 5-7 days with 16 hours of light at 27° C. Normally, this step requires transferring of selected tissue to solid first regeneration medium for further growth. This method eliminates this step. The partially regenerated tissue on the liquid first regeneration medium was then transferred to a Sorbarod plug placed in a liquid second regeneration medium (see Table 5 for composition) in a Sundae cup for full regeneration. This transfer step was eliminated if the inoculated embryos were cultured directly on the Sorbarod plug to begin with. In such a case, the liquid first regeneration medium was simply removed and replaced with the liquid second regeneration medium. The tissue was grown for about 2 weeks. Normally, this step requires transferring of the regenerating tissue from the first solid regeneration medium to the solid second regeneration medium for further growth. This method eliminates this step. Fully regenerated smaller corn plantlets in the Sorbarod plug were transferred to soil directly. Normally, this step requires transferring a fully regenerated smaller plantlet from the solid second regeneration medium to the solid rooting medium 1084 (see Table 5 for composition) for further growth. This method eliminates this step. The developing plantlets were hardened off in a growth chamber at 27° C., 80% humidity, and low light intensity for about 1 week and then transferred to a greenhouse and grown under standard greenhouse conditions and tested for the presence of CP4 gene. Table 6 shows the production of transgenic corn using liquid culture in combination with felt and Sorbarod plug and by eliminating several transfer steps.

A high throughput transformation system for corn is developed in which containers are manipulated by robotic arms on a freely configurable work table that include usable incubators and shakers in addition to standard lab ware. Various liquid handling tools equipped with one or more pipetting tips are used to provide the fresh medium and remove the expensed medium. Work table, robotic arms, and the liquid handling tools are controlled by software via a computer. Alternatively, liquid medium for selecting and regenerating the transformed cell can be provided to the container via one or more tube connected to a medium storage vessel and removed via one or more tubes connected to a waste vessel. The provision and removal of the liquid medium is controlled manually or mechanically.

TABLE 6

Corn transformation frequency (TF) using liquid medium in combination with different matrices.

| | Medium | Matrix | Culture conditions during selection | # Explants | # Plants regenerated | % TF |
|---|---|---|---|---|---|---|
| Ear 1 | Solid | None | 14-21 d, 27° C. dark | 20 | 2 | 10 |
| | Solid | None | 10-d, 30° C. dark; 7-d, 28° C. light | 20 | 3 | 15 |
| | Liquid | plug | 10-d, 30° C. dark; 7-d, 28° C. light | 72 | 5 | 6.9 |
| | Liquid | felt/plug | 10-d, 30° C. dark; 7-d, 28° C. light | 63 | 5 | 7.9 |
| Ear 2 | Solid | None | 14-21 d, 27° C. dark | 20 | 2 | 10 |
| | Solid | None | 10-d, 30° C. dark; 7-d, 28° C. light | 20 | 4 | 20 |
| | Liquid | plug | 10-d, 30° C. dark; 7-d, 28° C. light | 72 | 7 | 9.7 |
| | Liquid | felt/plug | 10-d, 30° C. dark; 7-d, 28° C. light | 63 | 8 | 12.7 |
| Ear 3 | Solid | None | 14-21 d, 27° C. dark | 30 | 6 | 20 |
| | Solid | None | 10-d, 30° C. dark; 7-d, 28° C. light | 30 | 9 | 30 |
| | Liquid | plug | 10-d, 30° C. dark; 7-d, 28° C. light | 70 | 7 | 10 |
| | Liquid | felt/plug | 10-d, 30° C. dark; 7-d, 28° C. light | 63 | 8 | 12.7 |

Transformation frequency is calculated as the percent of cultured embryos that produced transgenic plants.

REFERENCES

The following references, to the extent that they provide exemplary procedural or other details supplementary to those set forth herein, are specifically incorporated herein by reference.

U.S. Pat. No. 5,159,135
U.S. Pat. No. 5,362,865
U.S. Pat. No. 5,569,834
U.S. Pat. No. 5,106,739
U.S. Pat. No. 5,107,065
U.S. Pat. No. 5,627,061
U.S. Pat. No. 5,633,435
U.S. Pat. No. 6,506,559
U.S. Appln. Publn. 2002/0168707
U.S. Appln. Publn. 2004/0244075
U.S. application Ser. No. 09/423,143
Bird et al., *Biotech Gen. Engin. Rev.*, 9:207-227, 1991.
Broothaerts et al, *Nature*, 433:630, 2005.
Cheng et al., *Dev. Biol.-Plant*, 39:595-604, 2003.
Chu et al., *Scientia. Sinica.*, 18:659, 1975.
Dekeyser et al., *Plant Physiol.*, 90:217-223, 1989.
Della-Cioppa et al., *Bio/Technology*, 5 579-584, 1987.
Duncan et al., *Planta*, 165:322-332, 1985.
Duncan et al., *Planta*, 165:322-332, 1985.
European Patent Appln. 0385 962
Gamborg et al., *Exp. Cell Res.*, 50:151, 1968.
Gibson and Shillitoe, *Mol. Biotech.*, 7:125-137, 1997.
Jefferson, *Plant Mol. Biol. Rep.*, 5:287-405, 1987.
Linsmaier and Skoog, *Physiol. Plant.*, 18:100, 1965.
McCown and Lloyd, *HortScience*, 16:453, 1981.
Murashige and Skoog, *Physiol. Plant*, 15:473-497, 1962.
Nitsch and Nitsch, *Science*, 163:85-87, 1969.
PCT Appln. WO 09/084,942
PCT Appln. WO 09/127,735
PCT Appln. WO 97/48814
PCT Appln. WO 98/53083
PCT Appln. WO 99/53050
PCT Appln. WO 99/61631

Sambrook et al., In: *Molecular Cloning*, A Laboratory Manual, 1989.

Sambrook and Russell, "Molecular Cloning: A Laboratory Manual", 3rd edition, Cold Spring Harbor Laboratory Press, NY, 2001.

Schenk and Hildebrandt, *Can. J. Bot.,* 50:199-204, 1972.

Southern, *Mol. Biol.* 98:503-517, 1975.

Uchimiya and Murashige, *Plant Physiol.,* 15:473, 1962.

What is claimed:

1. A method for producing a transformable and embryogenic corn cell culture comprising:
   a) obtaining a Type II callus from corn embryos;
   b) initiating a cell suspension culture from cells of the callus: and
   c) culturing the cell suspension for about 5 days to 30 days in a liquid medium to produce the cell culture, wherein the cell culture is transferred to fresh growth media every 2-3 days; and
   wherein undesirable cell types are removed from the cell culture during transfer to fresh growth media.

2. The method of claim 1, wherein the cell suspension is cultured for about 5 to about 15 days.

\* \* \* \* \*